US012799543B2

(12) United States Patent
Tateda et al.

(10) Patent No.: US 12,799,543 B2
(45) Date of Patent: Nov. 17, 2026

(54) METHOD FOR AMPLIFYING TARGET GENE HAVING SPECIFIC GC CONTENT

(71) Applicants: Denka Company Limited, Tokyo (JP); Toho University, Tokyo (JP)

(72) Inventors: Kazuhiro Tateda, Tokyo (JP); Yuya Miyatake, Tokyo (JP)

(73) Assignees: Denka Company Limited, Tokyo (JP); Toho University, Tokyo (JP)

( * ) Notice: Subject to any disclaimer, the term of this patent is extended or adjusted under 35 U.S.C. 154(b) by 483 days.

(21) Appl. No.: 18/552,083

(22) PCT Filed: Mar. 24, 2022

(86) PCT No.: PCT/JP2022/013805

§ 371 (c)(1),
(2) Date: Sep. 22, 2023

(87) PCT Pub. No.: WO2022/202954

PCT Pub. Date: Sep. 29, 2022

(65) Prior Publication Data

US 2024/0175095 A1 May 30, 2024

(30) Foreign Application Priority Data

Mar. 24, 2021 (JP) ................................ 2021-049853

(51) Int. Cl.
*C12Q 1/689* (2018.01)
*C12Q 1/686* (2018.01)

(52) U.S. Cl.
CPC ............ *C12Q 1/689* (2013.01); *C12Q 1/686* (2013.01)

(58) Field of Classification Search
CPC ....... C12Q 1/686; C12Q 1/689; C12Q 1/6844
See application file for complete search history.

(56) References Cited

U.S. PATENT DOCUMENTS 10,302,640 B2 * 5/2019 Tsao ................ G01N 33/54326
2015/0275276 A1 10/2015 Wallach et al.

FOREIGN PATENT DOCUMENTS

CN 106399568 A 2/2017
CN 107338315 A 11/2017
CN 109554477 A 4/2019
CN 109778321 A 5/2019
(Continued)

OTHER PUBLICATIONS

English translation of CN 107338315 B (created Jan. 16, 2026) (Year: 2026).*
(Continued)

*Primary Examiner* — Samuel C Woolwine
*Assistant Examiner* — Kara N Kovach
(74) *Attorney, Agent, or Firm* — Foley & Lardner LLP

(57) ABSTRACT

The present invention provides a method for amplifying, in a reaction solution, at least one target gene having a GC content of at least 60%, wherein the method contains a step of amplifying a specific base sequence in a target gene by using a primer set consisting of a first primer and a second primer for target gene amplification, and wherein one primer in the primer set is added to the reaction solution at a molar ratio higher than the other primer and neither primer is a hot start primer that contains an inactivating chemical modification that is restored by an action of an activating enzyme.

17 Claims, 4 Drawing Sheets

Specification includes a Sequence Listing.

(56) References Cited

FOREIGN PATENT DOCUMENTS

| | | | | | |
|---|---|---|---|---|---|
| CN | 110106265 A | | 8/2019 | | |
| CN | 110564843 A | | 12/2019 | | |
| CN | 110878370 A | | 3/2020 | | |
| CN | 107338315 B | * | 7/2020 | ............ | C12Q 1/686 |
| CN | 111793676 A | | 10/2020 | | |
| JP | 2015-536653 A | | 12/2015 | | |

OTHER PUBLICATIONS

Gentile et al., "Verification of monoplex and multiplex linear-after-the-exponential PCR gene-specific sepsis assays using clinical isolates," Journal of Applied Microbiology, 2012, 114:586-594.

Miller et al., "In Situ synthesized Virulence and Marker Gene Biochip for Detection of Bacterial Pathogens in Water," Applied and Environmental Microbiology, 2008, 74(7):2200-2209.

Rice et al., "Design of a single-tube, endpoint, linear-after-the-exponential-PCR assay for 17 pathogens associated with sepsis," Journal of Applied Microbiology, 2012, 114:457-469.

Poulson et al., "Closed-tube genotyping of apolipoprotein E by isolated-probe PCR with multiple unlabeled probes and high-resolution DNA melting analysis," BioTechniques, Jul. 2007, 43(1):87-91.

* cited by examiner

Fig. 1

| | | | |
|---|---|---|---|
| Pseudomonas aeruginosa E6130952 | 1 | TTACTTCTTCAGCTCGACGCGACGGTTCTGAGCCCAGGACTGCTCGTCGTGGCCGGTAGCGACCGGACGCTCTTTACCATAGGAAACCAGTTCCAGCTGG | 100 |
| Pseudomonas aeruginosa NCTC10332 | 1 | TTACTTCTTCAGCTCGACGCGACGGTTCTGAGCCCAGGACTGCTCGTCGTGGCCGGTAGCGACCGGACGCTCTTTACCATAGGAAACCAGTTCCAGCTGG | 100 |
| Pseudomonas aeruginosa PAO1 | 1 | TTACTTCTTCAGCTCGACGCGACGGTTCTGAGCCCAGGACTGCTCGTCGTGGCCGGTAGCGACCGGACGCTCTTTACCATAGGAAACCAGTTCCAGCTGG | 100 |
| Pseudomonas aeruginosa E6130952 | 101 | GCCGGCGAAACGCCCTGCAGCACCAGGTAGCGCTGAACGGCCTTGGCACGACGCTCGCCCAGAGCCATGTTGTACTCGCGGGTGCCGCGTTCGTCGGTGT | 200 |
| Pseudomonas aeruginosa NCTC10332 | 101 | GCCGGCGAAACGCCCTGCAGCACCAGGTAGCGCTGAACGGCCTTGGCACGACGCTCGCCCAGAGCCATGTTGTACTCGCGGGTGCCGCGTTCGTCGGTGT | 200 |
| Pseudomonas aeruginosa PAO1 | 101 | GCCGGCGAAACACCCTGCAGCACCAGGTAGCGCTGAACGGCCTTGGCACGACGCTCGCCCAGAGCCATATTGTACTCGCGGGTGCCGCGTTCGTCGGTGT | 200 |
| Pseudomonas aeruginosa E6130952 | 201 | GGCCTTCCAGCACTACGCGCTGACCGCTGCCTTTCAGGTCTTTCGCGTGTACGTCCAGAGCGCGCATGGCTTCCGGCTTCAGGTCGGAGCTGTCGTACTC | 300 |
| Pseudomonas aeruginosa NCTC10332 | 201 | GGCCTTCCAGCACTACGCGCTGACCGCTGCCTTTCAGGTCTTTCGCGTGTACGTCCAGAGCGCGCATGGCTTCCGGCTTCAGGTCGGAGCTGTCGTACTC | 300 |
| Pseudomonas aeruginosa PAO1 | 201 | GGCCTTCCAGCACTACGCGCTGACCGCTGCCTTTCAGGTCTTTCGCGTGTACGTCCAGAGCGCGCATGGCTTCCGGCTTCAGGTCGGAGCTGTCGTACTC | 300 |
| Pseudomonas aeruginosa E6130952 | 301 | GAAGTAGAAGGTGGTGATCGCACGCAGAGCGGCTTCGTCGCTCAGGCTGCCGTCAACGGCACCGCTGTTGGCGCCATAGCCTGCGTTCGGGTCGACGCCG | 400 |
| Pseudomonas aeruginosa NCTC10332 | 301 | GAAGTAGAAGGTGGTGATCGCACGCAGAGCGGCTTCGTCGCTCAGGCTGCCGTCAACGGCACCGCTGTTGGCGCCATAGCCTGCGTTCGGGTCGACGCCG | 400 |
| Pseudomonas aeruginosa PAO1 | 301 | GAAGTAGAAGGTGGTGATCGCACGCAGAGCGGCTTCGTCGCTCAGGCTGCCGTCAACGGCACCGCTGTTGGCGCCATAGCCTGCGTTCGGGTCGACGCCG | 400 |
| Pseudomonas aeruginosa E6130952 | 401 | CCATTGGCACCTTCACCGGAAGCATCGCCGCCCTTGGAGGAGCAACCCACAGCCACAGCCATGGCCAGAGCCAGCGCAGCAAATTTGCCGAATTTCAGCA | 500 |
| Pseudomonas aeruginosa NCTC10332 | 401 | CCATTGGCACCTTCACCGGAAGCATCGCCGCCCTTGGAGGAGCAACCCACAGCCACAGCCATGGCCAGAGCCAGCGCAGCAAATTTGCCGAATTTCAGCA | 500 |
| Pseudomonas aeruginosa PAO1 | 401 | CCATTGGCACCTTCACCGGAAGCATCGCCGCCCTTGGAGGAGCAACCCACAGCCACAGCCATGGCCAGAGCCAGCGCAGCAAATTTGCCGAATTTCAGCA | 500 |
| Pseudomonas aeruginosa E6130952 | 501 | TTTCCAT | 507 |
| Pseudomonas aeruginosa NCTC10332 | 501 | TTTCCAT | 507 |
| Pseudomonas aeruginosa PAO1 | 501 | TTTCCAT | 507 |

SEQUENCE LISTING

```
<160> NUMBER OF SEQ ID NOS: 24

<210> SEQ ID NO 1
<211> LENGTH: 507
<212> TYPE: DNA
<213> ORGANISM: Pseudomonas aeruginosa strain E6130952

<400> SEQUENCE: 1

ttacttcttc agctcgacgc gacggttctg agcccaggac tgctcgtcgt ggccggtagc      60

gaccggacgc tctttaccat aggaaaccag ttccagctgg gccggcgaaa cgccctgcag     120

caccaggtag cgctgaacgg ccttggcacg acgctcgccc agagccatgt tgtactcgcg     180

ggtgccgcgt tcgtcggtgt ggccttccag cactacgcgc tgaccgctgc ctttcaggtc     240

tttcgcgtgt acgtccagag cgcgcatggc ttccggcttc aggtcggagc tgtcgtactc     300

gaagtagaag gtggtgatcg cacgcagagc ggcttcgtcg ctcaggctgc cgtcaacggc     360

accgctgttg gcgccatagc ctgcgttcgg gtcgacgccg ccattggcac cttcaccgga     420
```

-continued

```
agcatcgccg cccttggagg agcaacccac agccacagcc atggccagag ccagcgcagc    480

aaatttgccg aatttcagca tttccat                                        507


<210> SEQ ID NO 2
<211> LENGTH: 507
<212> TYPE: DNA
<213> ORGANISM: Pseudomonas aeruginosa strain NCTC10332

<400> SEQUENCE: 2

ttacttcttc agctcgacgc gacggttctg agcccaggac tgctcgtcgt ggccggtagc     60

gaccggacgc tctttaccat aggaaaccag ttccagctgg gccggcgaaa cgccctgcag    120

caccaggtag cgctgaacgg ccttggcacg acgctcgccc agagccatgt tgtactcgcg    180

ggtgccgcgt tcgtcggtgt ggccttccag cactacgcgc tgaccgctgc ctttcaggtc    240

tttcgcgtgt acgtccagag cgcgcatggc ttccggcttc aggtcggagc tgtcgtactc    300

gaagtagaag gtggtgatcg cacgcagagc ggcttcgtcg ctcaggctgc cgtcaacggc    360

accgctgttg gcgccatagc ctgcgttcgg gtcgacgccg ccattggcac cttcaccgga    420

agcatcgccg cccttggagg agcaacccac agccacagcc atggccagag ccagcgcagc    480

aaatttgccg aatttcagca tttccat                                        507


<210> SEQ ID NO 3
<211> LENGTH: 507
<212> TYPE: DNA
<213> ORGANISM: Pseudomonas aeruginosa strain PAO1

<400> SEQUENCE: 3

ttacttcttc agctcgacgc gacggttctg agcccaggac tgctcgtcgt ggccggtagc     60

gaccggacgc tctttaccat aggaaaccag ttccagctgg gccggcgaaa caccctgcag    120

caccaggtag cgctgaacgg ccttggcacg acgctcgccc agagccatat tgtactcgcg    180

ggtgccgcgt tcgtcggtgt ggccttccag cactacgcgc tgaccgctgc ctttcaggtc    240

tttcgcgtgt acgtccagag cgcgcatggc ttccggcttc aggtcggagc tgtcgtactc    300

gaagtagaag gtggtgatcg cacgcagagc ggcttcgtcg ctcaggctgc cgtcaacggc    360

accgctgttg gcgccatagc ctgcgttcgg gtcgacgccg ccattggcac cttcaccgga    420

agcatcgccg cccttggagg agcaacccac agccacagcc atggccagag ccagcgcagc    480

aaatttgccg aatttcagca tttccat                                        507


<210> SEQ ID NO 4
<211> LENGTH: 18
<212> TYPE: DNA
<213> ORGANISM: Artificial Sequence
<220> FEATURE:
<223> OTHER INFORMATION: Forward primer for Pseudomonas aeruginosa

<400> SEQUENCE: 4

ggtaaagagc gtccggtc                                                   18


<210> SEQ ID NO 5
<211> LENGTH: 19
<212> TYPE: DNA
<213> ORGANISM: Artificial Sequence
<220> FEATURE:
<223> OTHER INFORMATION: Reverse primer for Pseudomonas aeruginosa

<400> SEQUENCE: 5

ttacttcttc agctcgacg                                                  19
```

<210> SEQ ID NO 6
<211> LENGTH: 25
<212> TYPE: DNA
<213> ORGANISM: Artificial Sequence
<220> FEATURE:
<223> OTHER INFORMATION: Probe for Pseudomonas aeruginosa

<400> SEQUENCE: 6 ttttttttt ggtaaagagc gtccg 25

<210> SEQ ID NO 7
<211> LENGTH: 20
<212> TYPE: DNA
<213> ORGANISM: Artificial Sequence
<220> FEATURE:
<223> OTHER INFORMATION: Forward primer for Staphylococcus epidermidis

<400> SEQUENCE: 7
tacatyccaa ctccagaacg 20

<210> SEQ ID NO 8
<211> LENGTH: 20
<212> TYPE: DNA
<213> ORGANISM: Artificial Sequence
<220> FEATURE:
<223> OTHER INFORMATION: Reverse primer for Staphylococcus epidermidis

<400> SEQUENCE: 8
actttgattt gaccacgttc 20

<210> SEQ ID NO 9
<211> LENGTH: 25
<212> TYPE: DNA
<213> ORGANISM: Artificial Sequence
<220> FEATURE:
<223> OTHER INFORMATION: Probe for Staphylococcus epidermidis

<400> SEQUENCE: 9 tttttttta accattcatg atgcc 25

<210> SEQ ID NO 10
<211> LENGTH: 20
<212> TYPE: DNA
<213> ORGANISM: Artificial Sequence
<220> FEATURE:
<223> OTHER INFORMATION: Forward primer for Proteus mirabilis

<400> SEQUENCE: 10
caactcacta yggtcgtgtg 20

<210> SEQ ID NO 11
<211> LENGTH: 22
<212> TYPE: DNA
<213> ORGANISM: Artificial Sequence
<220> FEATURE:
<223> OTHER INFORMATION: Reverse primer for Proteus mirabilis

<400> SEQUENCE: 11
catctgttac agcgttgttt tc 22

<210> SEQ ID NO 12
<211> LENGTH: 25
<212> TYPE: DNA
<213> ORGANISM: Artificial Sequence
<220> FEATURE:

<223> OTHER INFORMATION: Probe for Proteus mirabilis

<400> SEQUENCE: 12
tttttttttt agaaacgcct taccg 25

<210> SEQ ID NO 13
<211> LENGTH: 23
<212> TYPE: DNA
<213> ORGANISM: Artificial Sequence
<220> FEATURE:
<223> OTHER INFORMATION: Forward primer for Acinetobacter baumannii

<400> SEQUENCE: 13
tgatctgacg aagacacatt aac 23

<210> SEQ ID NO 14
<211> LENGTH: 22
<212> TYPE: DNA
<213> ORGANISM: Artificial Sequence
<220> FEATURE:
<223> OTHER INFORMATION: Reverse primer for Acinetobacter baumannii

<400> SEQUENCE: 14
atttcagttt agagcactgt gc 22

<210> SEQ ID NO 15
<211> LENGTH: 25
<212> TYPE: DNA
<213> ORGANISM: Artificial Sequence
<220> FEATURE:
<223> OTHER INFORMATION: Probe for Acinetobacter baumannii

<400> SEQUENCE: 15 tttttgaat ttagattgaa gctgt 25

<210> SEQ ID NO 16
<211> LENGTH: 78
<212> TYPE: DNA
<213> ORGANISM: Pseudomonas aeruginosa

<400> SEQUENCE: 16
ttacttcttc agctcgacgc gacggttctg agcccaggac tgctcgtcgt ggccggtagc 60
gaccggacgc tctttacc 78

<210> SEQ ID NO 17
<211> LENGTH: 122
<212> TYPE: DNA
<213> ORGANISM: Staphylococcus epidermidis

<400> SEQUENCE: 17
tacattccaa ctccagaacg tgattctgac aaaccattca tgatgccagt tgaggacgta 60
ttctcaatca ctggtcgtgg tactgttgct acaggccgtg ttgaacgtgg tcaaatcaaa 120
gt 122

<210> SEQ ID NO 18
<211> LENGTH: 150
<212> TYPE: DNA
<213> ORGANISM: Proteus mirabilis

<400> SEQUENCE: 18
caactcacta tggtcgtgtg tgtccaatcg aaacacctga aggtccaaat atcggtctga 60
ttaactcatt atctgtttat gcacagacta acgagtacgg attcttagaa acgccttacc 120
gtgttgtaga aaacaacgct gtaacagatg 150

<210> SEQ ID NO 19
<211> LENGTH: 198
<212> TYPE: DNA
<213> ORGANISM: Acinetobacter baumannii

<400> SEQUENCE: 19
tgatctgacg aagacacatt aactcattaa cagattggca aaattgagtc tgaaataaat 60
tgttcactca agagtttagg ttaagcaatt aatctagatg aattgagaac tagcaaatta 120
actgaatcaa gcgttttggt atgtgaattt agattgaagc tgtacggtgc ttaagtgcac 180
agtgctctaa actgaaat 198

<210> SEQ ID NO 20
<211> LENGTH: 25
<212> TYPE: DNA
<213> ORGANISM: Artificial Sequence
<220> FEATURE:
<223> OTHER INFORMATION: Primer for Enterococcus casseliflavus

<400> SEQUENCE: 20
ttcaattaaa tttggtaatt ccaat 25

<210> SEQ ID NO 21
<211> LENGTH: 24
<212> TYPE: DNA
<213> ORGANISM: Artificial Sequence
<220> FEATURE:
<223> OTHER INFORMATION: Primer for Enterococcus casseliflavus

<400> SEQUENCE: 21
tcaatcaaat tcggtaattc yaat 24

<210> SEQ ID NO 22
<211> LENGTH: 23
<212> TYPE: DNA
<213> ORGANISM: Artificial Sequence
<220> FEATURE:
<223> OTHER INFORMATION: Primer for Enterococcus casseliflavus

<400> SEQUENCE: 22
cgatcaaatt yggtaattcc aac 23

<210> SEQ ID NO 23
<211> LENGTH: 18
<212> TYPE: DNA
<213> ORGANISM: Artificial Sequence
<220> FEATURE:
<223> OTHER INFORMATION: Primer for Enterococcus casseliflavus

<400> SEQUENCE: 23
arcttggctg gacacgta 18

<210> SEQ ID NO 24
<211> LENGTH: 15
<212> TYPE: DNA
<213> ORGANISM: Artificial Sequence
<220> FEATURE:
<223> OTHER INFORMATION: Probe for Enterococcus casseliflavus

<400> SEQUENCE: 24
gcttctacgt tctcg 15

METHOD FOR AMPLIFYING TARGET GENE HAVING SPECIFIC GC CONTENT

CROSS-REFERENCE TO RELATED APPLICATIONS

This application is the U.S. National Stage of PCT/JP2022/013805, filed Mar. 24, 2022, which claims priority to JP 2021-049853, filed Mar. 24, 2021.

The instant application contains a Sequence Listing which has been submitted in ASCII format via EFS-WEB and is hereby incorporated by reference in its entirety. Said ASCII copy, created on Sep. 21, 2023, is named 120847-0125_sequence.txt and is 7,493 bytes.

TECHNICAL FIELD

The present invention generally relates to, for instance, a method for amplifying, in a reaction solution, a target gene having a specific GC content by using asymmetric PCR.

*Pseudomonas aeruginosa* is a resident bacterium present on the epithelium and in the intestinal tract of humans and is a typical bacterial species associated with opportunistic infections. Multidrug-resistant *Pseudomonas aeruginosa*, having acquired drug resistance, is a frequent cause of nosocomial infection outbreaks. *Pseudomonas aeruginosa* is thus a bacterial species that is drawing the attention of medical institutions.

CITATION LIST

Patent Document

Patent Document 1: Japanese Unexamined Patent Application Publication No. 2015-536653

SUMMARY

Technical Problem

It is generally known that the genes carried by an organism have a species-specific constituent base composition and GC content. *Pseudomonas aeruginosa* is a bacterium characterized by a high GC content; for example, the result of an analysis of the complete genome of the PA01 strain was a GC content of 66.6% (Stover, C. K., Pham, X. Q., Erwin, A. L., Mizoguchi, S. D., Warrener, P., Hickey, M. J., Brinkman, F. S., Hufnagle, W. O., Kowalik, D. J., Lagrou, M. et al. 2000. Complete genome sequence of *Pseudomonas aeruginosa* PA01, an opportunistic pathogen. Nature 406: 959-964.).

However, it has been found that, when a bacterium having high GC content genes, such as *Pseudomonas aeruginosa*, is a target, the amount of synthesis of the PCR product of the target gene declines and the detection sensitivity declines. The decline in detection sensitivity becomes a particular problem for methods in which a target gene is to be amplified at the same time as amplification of a gene in a sample that contains various bacterial species to be differentiated in addition to the target gene and the target bacterial species that contains the same. Such a simultaneous amplification of different genes is frequently referred to as multiplex PCR, and is a procedure that can amplify a plurality of gene fragments from a single template DNA in a single reaction system. This multiplex PCR, which exhibits an excellent throughput, can also amplify respective gene fragments from a plurality of template DNAs present in a reaction system and has become an indispensable technique among genetic diagnostic technologies.

Solution to Problem

As a result of extensive and intensive research in order to solve the aforementioned problem, the present inventors, by combining a technology for detecting a high GC content target gene (also referred to as the gene of interest (GOI)) with asymmetric PCR, created a comprehensive, highly sensitive, and highly specific technology that can simultaneously detect GOIs having a high GC content of at least 60%, as well as target genes not having a high GC content (GC content: 40 to 60%), and thus came to achieve the present invention.

That is, the present application comprises the following inventions.

[1] A method for amplifying, in a reaction solution, at least one target gene having a GC content of at least 60%, the method including a step of amplifying a specific base sequence in a target gene by using a primer set consisting of a first primer and a second primer target gene amplification, and wherein one primer in the primer set is added to the reaction solution at a molar ratio higher than the other primer and neither primer is a hot start primer that contains an inactivating chemical modification that is restored by an action of an activating enzyme.

[2] The method according to [1], wherein the reaction solution contains one or a plurality of genes that are not a target gene and wherein the method includes simultaneous amplification of both a target gene and the one or a plurality of genes that are not a target gene.

[3] The method according to [1] or [2], wherein the molar ratio of the primers in the primer set is 1:1.5 to 20.0.

[4] The method according to any of [1] to [3], wherein a target gene is a base sequence consisting of at least 13 consecutive bases in the genomic sequence of *Pseudomonas aeruginosa.*

[5] The method according to any of [1] to [4], wherein the first primer is a primer that hybridizes, under stringent conditions, with a base sequence described in any of SEQ ID NOs: 1 to 3 or with a base sequence provided by deletion, substitution, insertion, or addition of one or a plurality of bases in a base sequence described in any of SEQ ID NOs: 1 to 3, and the second primer is a primer that hybridizes, under stringent conditions, with a complementary strand sequence for a base sequence described in any of SEQ ID NOs: 1 to 3 or with a base sequence provided by the deletion, substitution, insertion, or addition of one or a plurality of bases in a complementary strand sequence for a base sequence described in any of SEQ ID NOs: 1 to 3.

[6] The method according to any of [1] to [5], wherein the first primer is an oligonucleotide consisting of at least 13 consecutive bases in the base sequence described in SEQ ID NO: 4 or in a base sequence provided by the deletion, substitution, insertion, or addition of one or a plurality of bases in the base sequence described in SEQ ID NO: 4.

[7] The method according to any of [1] to [6], wherein the second primer is an oligonucleotide consisting of at least 13 consecutive bases in the base sequence described in SEQ ID NO: 5 or in a base sequence provided by the deletion, substitution, insertion, or addition of one or a plurality of bases in the base sequence described in SEQ ID NO: 5.

[8] The method according to any of [1] to [7], wherein a primer is labeled with biotin.

[9] The method according to any of [1] to [8], wherein the primer with a higher molar ratio is labeled with biotin.

[10] A method of detecting, in one reaction solution, at least one target gene having a GC content greater than 60%, the method including a step of detecting a target gene by using a probe that is complementary to a single strand of a target gene that has been amplified by the method described in any of [1] to [9].

[11] The method according to [10], wherein the probe is complementary to a single strand of the target gene that has been amplified by the primer with the higher molar ratio.

[12] The method according to or [11], wherein a target gene is detected through occurrence of complementary double-stranded gene formation from the probe and a single strand of the target gene.

[13] The method according to any of [1] to [12], wherein a target gene originates from *Pseudomonas aeruginosa* and a bacterial gene from other than *Pseudomonas aeruginosa* is differentiated from *Pseudomonas aeruginosa.*

[14] The method according to any of to [13], wherein the probe is immobilized on a detection substrate material.

[15] The method according to any of to [14], wherein the probe is labeled.

[16] The method according to any of to [15], wherein a probe nucleic acid contains an oligonucleotide consisting of at least 13 consecutive bases in the base sequence described in SEQ ID NO: 6 or in a base sequence provided by the deletion, substitution, insertion, or addition of one or a plurality of bases in the base sequence described in SEQ ID NO: 6.

[17] The method according to any of to [16], wherein a detection substrate material is a coded microcarrier.

[18] The method according to [17], wherein the microcarrier contains:

(a) a layer that is a substantially transparent polymer layer having a first surface and a second surface, with the first and second surfaces being parallel to each other;

(b) a layer that is a substantially opaque polymer layer, this substantially opaque polymer layer being affixed to the first surface of the substantially transparent polymer layer and encompassing a central region of the substantially transparent polymer layer, and the substantially opaque polymer layer containing a two-dimensional shape that represents an analog code; and (c) a capture agent for capturing an analyte, the capture agent being attached to at least one of the first surface and the second surface of the substantially transparent polymer layer, in at least the central region of the substantially transparent polymer layer.

[19] A primer set, consisting of a first primer and a second primer, for detecting the presence of at least one target gene having a GC content of at least 60%, wherein the first primer is an oligonucleotide consisting of at least 13 consecutive bases in the base sequence described in SEQ ID NO: 4 or in a base sequence provided by deletion, substitution, insertion, or addition of one or a plurality of bases in the base sequence described in SEQ ID NO: 4, and the second primer is an oligonucleotide consisting of at least 13 consecutive bases in the base sequence described in SEQ ID NO: 5 or in a base sequence provided by the deletion, substitution, insertion, or addition of one or a plurality of bases in the base sequence described in SEQ ID NO: 5.

[20] The primer set according to [19], wherein a target gene is a base sequence consisting of at least 13 consecutive bases in the genomic sequence of *Pseudomonas aeruginosa.*

[21] The primer set according to or [20], wherein the first primer is a primer that hybridizes, under stringent conditions, with a base sequence described in any of SEQ ID NOs: 1 to 3 or with a base sequence provided by the deletion, substitution, insertion, or addition of one or a plurality of bases in a base sequence described in any of SEQ ID NOs: 1 to 3, and the second primer is a primer that hybridizes, under stringent conditions, with a complementary strand sequence for a base sequence described in any of SEQ ID NOs: 1 to 3 or with a base sequence provided by the deletion, substitution, insertion, or addition of one or a plurality of bases in a complementary strand sequence for a base sequence described in any of SEQ ID NOs: 1 to 3.

[22] The primer set according to any of to [21], wherein the first primer is an oligonucleotide consisting of at least 13 consecutive bases in the base sequence described in SEQ ID NO: 4 or in a base sequence provided by the deletion, substitution, insertion, or addition of one or a plurality of bases in the base sequence described in SEQ ID NO: 4.

[23] The primer set according to any of to [22], wherein the second primer is an oligonucleotide consisting of at least 13 consecutive bases in the base sequence described in SEQ ID NO: 5 or in a base sequence provided by the deletion, substitution, insertion, or addition of one or a plurality of bases in the base sequence described in SEQ ID NO: 5.

Advantageous Effects of Invention

The present invention enables the highly sensitive detection of high GC content genes through the use of asymmetric PCR.

BRIEF DESCRIPTION OF DRAWINGS

FIG. 1 shows the results of multiple sequence alignment for the oprL gene of the E6130952 strain, NCTC10332 strain, and PAO1 strain of *P. aeruginosa* (SEQ ID NOs: 1, 2, 3).

DESCRIPTION OF EMBODIMENTS

Figure 2:
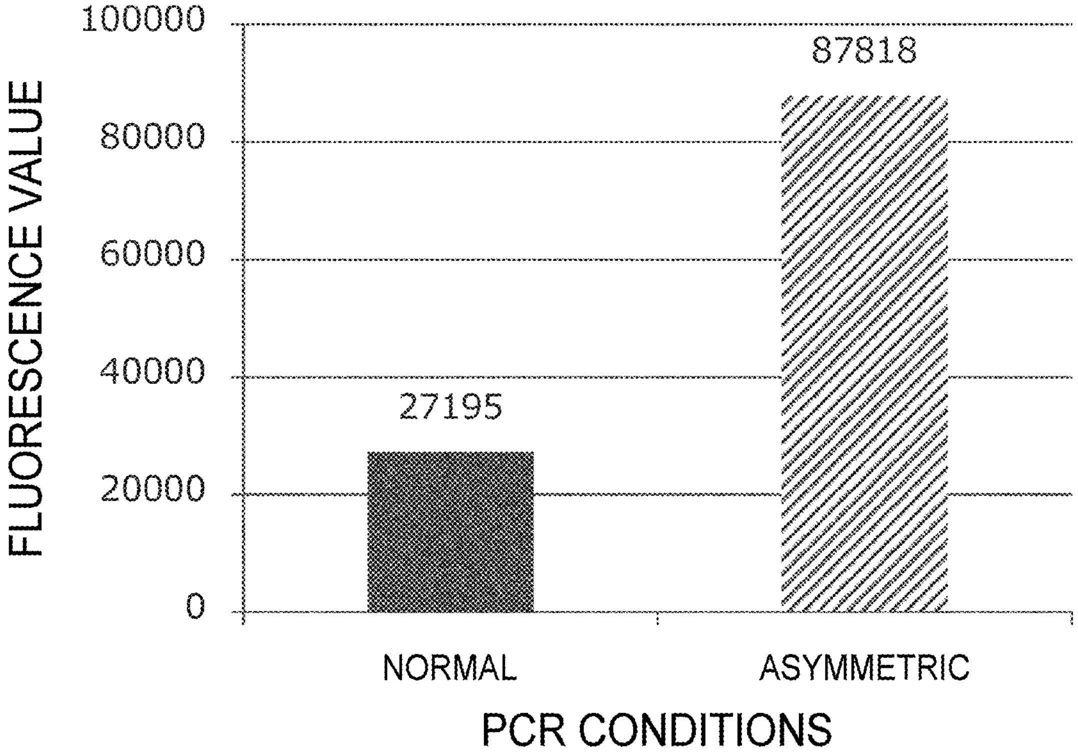
FIG. 2 shows the results of a comparison of the fluorescence values in normal PCR and asymmetric PCR carried out on a template of genomic DNA extracted from *P. aeruginosa* strain JCM14847.

Embodiments of the present invention (referred to hereafter as "the present embodiments") are described in the following, but this should not be construed as limiting the scope of the present invention to the following embodiments.

(Gene Amplification•Detection Methods)

A first aspect provides a method for amplifying, in a reaction solution, at least one target gene having a GC content of at least 60%. This amplification method can contain a step of amplifying a specific base sequence in a target gene using a primer set containing a first primer and a second primer for target gene amplification, and can contain other optional steps. The amplification step includes a step of bringing the primer set into contact with a target gene. The reaction solution may contain one or a plurality of genes that are not a target gene, in which case the target gene(s) and the one or a plurality of non-target genes are simultaneously submitted to the amplification reaction.

The target gene, also referred to as a gene of interest (GOI), may be any gene that has a GC content of at least 60%. When the amplification reaction is carried out using multiplex PCR, a target gene, among the plurality of genes that are to be amplified, is preferably a gene having a relatively high GC content. The GC content is the proportion (%) for the G base and C base in the DNA strand constituting the target gene and is determined by performing sequence analysis of the target gene. In addition to *Pseudomonas aeruginosa*, bacteria having a target gene with at least 60% can be exemplified by *Mycobacterium tuberculosis* (65.86%), *Propionibacterium acnes* (60.3%), and *Bifidobacterium* spp. (*Bifidobacterium longum* at 60.84% and *Bifidobacterium animalis* at 61.36%), but there is no limitation to these bacteria. The oprL gene (GC content: 62.3%) from *Pseudomonas aeruginosa* is an example of a target gene. The oprL gene is a gene in *Pseudomonas aeruginosa* that codes for a precursor to peptidoglycan lipoprotein.

The target gene amplification step is carried out using asymmetric PCR under amplification conditions. For example, the molar ratio of the primers added to the reaction solution for target gene amplification is managed so one primer has a higher concentration than the other primer. Japanese Unexamined Patent Application Publication No. 2015-536653 (supra) discloses, for the primers used in asymmetric PCR, hot start primers that contain an inactivating chemical modification that is restored by the action of an activating enzyme, but the primer set used in the present gene amplification method does not contain an inactivating chemical modification that is restored by the action of an activating enzyme, as in such hot start primers (riboprimers). On the other hand, with regard to the primers used to amplify a gene that is not a target gene, these may be any primers and the added amounts of the forward primer and reverse primer may also be an equal molar ratio.

The molar ratio of the primers for target gene amplification should be able to efficiently amplify a target gene in comparison to normal PCR, but is not otherwise particularly limited; however, for example, it is adjusted as appropriate within the range of 1:1.5 to 20.0 in the reaction solution prior to amplification. From the standpoint of further increasing the fluorescence intensity, the molar ratio is preferably 1:1.5 to 3.5, more preferably 1.5 to 3.0, and still more preferably 1.5 to 2.5. For the case of target gene amplification under asymmetric PCR conditions, the single strand that is the amplification product of the primer added in excess is produced more abundantly than the single strand that is amplified by the other primer, and as a consequence the efficiency of formation of the complementary strand between this single strand and the probe is also increased. A plurality of target genes may be present, in which case it becomes necessary to prepare a different primer set for each different target gene.

With regard to the design of the primer sequence for target gene amplification, the individual skilled in the art can, referring to the sequence of the target gene to be amplified, make a determination as appropriate of an oligonucleotide sequence that will be complementary. The primers used in the asymmetric PCR preferably are produced so the Tm values of the forward primer and reverse primer are on the same level. For example, when a target gene is a gene from *Pseudomonas aeruginosa*, primers are synthesized that are complementary to a base sequence composed of at least 13 consecutive bases in the genomic sequence of *Pseudomonas aeruginosa*. The oprL gene, with a GC content of approximately 62%, is an example of a target gene in *Pseudomonas aeruginosa*. The oprL gene is one of the genes that encode outer membrane proteins, and its sequence differs from strain to strain. For example, the oprL genes for *Pseudomonas aeruginosa* strain E6130952, strain NCTC10332, and strain PAO1 have the base sequences given in SEQ ID NOs: 1, 2, and 3, respectively.

The oprL gene has the base sequence given in any of SEQ ID NOs: 1 to 3 or has a base sequence provided by the deletion, substitution, insertion, or addition of one or a plurality of bases in a base sequence given in any of SEQ ID NOs: 1 to 3, and encodes OprL protein.

Functioning as the forward primer, the first primer may have any sequence that is able to hybridize, under stringent conditions, with a base sequence described in any of SEQ ID NOs: 1 to 3 or with a base sequence provided by the deletion, substitution, insertion, or addition of one or a plurality of bases in a base sequence described in any of SEQ ID NOs: 1 to 3.

Functioning as the reverse primer, the second primer may have any sequence that is able to hybridize, under stringent conditions, with a complementary strand sequence for a base sequence described in any of SEQ ID NOs: 1 to 3 or with a base sequence provided by the deletion, substitution, insertion, or addition of one or a plurality of bases in a complementary strand sequence for a base sequence described in any of SEQ ID NOs: 1 to 3.

As used in the present Description, "stringent conditions" denotes conditions in which a so-called specific hybrid is formed and nonspecific hybrids are not formed, and, for example, can be determined as appropriate based on data such as, e.g., the length of the base sequence. For example, stringent conditions can be established with reference to Molecular Cloning (Fourth Edition, Cold Spring Harbor Laboratory Press, New York). Stringent conditions may also refer to conditions in which highly homologous (preferably identical) polynucleotides, for example, polynucleotides having a homology of at least 70%, preferably at least 80%, more preferably at least 90%, still more preferably at least 95%, and particularly preferably at least 99%, hybridize with each other, and polynucleotides that exhibit a homology lower than this do not hybridize with each other.

The following conditions are specific stringent conditions: incubation at approximately 42° C. to approximately 50° C. in a hybridization solution (50% formamide, 10×SSC (0.15 M NaCl, 15 mM sodium citrate, pH 7.0), 5×Denhardt's solution, 1% SDS, 10% dextran sulfate, 10 μg/mL denatured salmon sperm DNA, and 50 mM phosphate buffer (pH 7.5)) of a base sequence complementary to a desired base sequence with a sample for which the presence of the target gene or bacterial species having the target gene is suspected, and washing at approximately 65° C. to approximately 70° ° C. using 0.1×SSC and 0.1% SDS.

An example of a first primer targeted to the oprL gene of *Pseudomonas aeruginosa* is a first primer having the base sequence given in SEQ ID NO: 4 given below, or a first primer that has the same functionality as the base sequence given in SEQ ID NO: 4 while having a base sequence consisting of at least 13 consecutive bases in a base sequence provided by the deletion, substitution, insertion, or addition of one or a plurality of bases in the base sequence described in SEQ ID NO: 4.

```
                                        (SEQ ID NO: 4)
5'-GGTAAAGAGCGTCCGGTC-3'
```

An example of a second primer targeted to the oprL gene of *Pseudomonas aeruginosa* is a second primer having the base sequence given in SEQ ID NO: 5 given below, or a second primer that has the same functionality as the base sequence given in SEQ ID NO: 5 while having a base sequence consisting of at least 13 consecutive bases in a base sequence provided by the deletion, substitution, insertion, or addition of one or a plurality of bases in the base sequence described in SEQ ID NO: 5.

```
                                        (SEQ ID NO: 5)
5'-TTACTTCTTCAGCTCGACG-3'
```

The first and second primers can specifically amplify the entire region or a partial region of a target gene, thereby enabling discrimination from another gene. Or, the amplification product from the first and second primers can be submitted to melting curve analysis and the target gene (or bacterial species containing same) can also be differentiated from another gene (or other bacterial species containing same) by comparing the melting temperature of the amplification product from the first and second primers with the melting temperature of the amplification product provided by another primer set.

The GC content of genes deriving from bacterial species other than the bacterial species that is to be differentiated—these being genes other than the gene(s) present in the bacterial species whose differentiation is being pursued and more specifically being genes other than the target gene(s)—is not particularly limited, but is preferably less than 60%.

The primers for amplification of a gene that is not a target gene may have any length; for example, this length can be established as appropriate in the range of approximately 10 bases to approximately 35 bases, with at least 10 bases being preferred.

The ratio for primers for amplification of a gene that is not a target gene is not particularly limited, and may be the same or may differ. When a primer set is to be used in the asymmetric PCR method, adjustment may be made so the concentration of one primer is higher than the concentration of the other primer.

Bacteria that have a GC content of less than 60% can be exemplified by *Staphylococcus epidermidis, Proteus mirabilis*, and *Acinetobacter baumannii*, but there is no limitation to these. Other examples of microorganisms that have a GC content of less than 60% are as follows: genus *Citrobacter*, such as *Citrobacter koseri, Citrobacter freundii, Citrobacter braakii*, and *Citrobacter amalonaticus*; genus *Enterobacter*, such as *Enterobacter cloacae* and *Enterobacter asburiae; Escherichia coli*; genus *Klebsiella*, such as *Klebsiella aerogenes, Klebsiella oxytoca, Klebsiella pneumoniae*, and *Klebsiella variola; Serratia marcescens*; genus *Enterococcus*, such as *Enterococcus casseliflavus, Enterococcus faecalis*, and *Enterococcus faecium*; genus *Listeria*, such as *Listeria monocytogenes*; genus *Staphylococcus*, such as *Staphylococcus aureus* and *Staphylococcus hominis*; genus *Streptococcus*, such as *Streptococcus oralis, Streptococcus pneumoniae* and *Streptococcus pyogenes; Corynebacterium jeikeium; Neisseria meningitidis*; and genus *Candida*, such as *Candida albicans*.

The primer set for target gene amplification is not limited to the combination of a first and second primers, and may contain these first and second primers as well as other primers, for example, an additional primer, e.g., a third, fourth, fifth, and sixth primers. The detection sensitivity can be improved by the use of suitable additional primers. Such primers are presumably, for example, primers for the amplification of regions in the target gene that are different from the region that the first and second primers amplify.

The presence of a target gene, or bacterial species bearing it, contained in a sample can be detected by a nucleic acid amplification reaction using the primers described in the preceding. Target gene amplification and detection are preferably carried out in a single reaction solution from an efficiency standpoint. A label capable of specifically recognizing the amplification product may be used for detection of the amplification product after the nucleic acid amplification reaction. Such a label can be exemplified by fluorescent dyes, biotin, digoxigenin, and so forth. Either primer may be a labeled primer, but, in the case of a primer set used in asymmetric PCR, the primer with the higher molar ratio is preferably labeled. The labeling site is also not limited, but is preferably located, either directly or through a linker, at the 5'-end of the primer.

When a probe is used, a target gene can be detected by the occurrence of the formation of a complementary double-stranded gene between the probe and a single strand of the target gene that has been amplified by the asymmetric PCR. The probe is preferably designed to be complementary with the single strand of the target gene that has been amplified by the higher molar ratio primer. When fluorescence is used for the label, this fluorescence can be detected using, e.g., a fluorescence microscope, fluorescence plate reader, and so forth.

An example of a probe is the probe described in SEQ ID NO: 6, which captures the PCR product of *Pseudomonas aeruginosa* strain JCM14847. When the nucleic acid coding for the probe has the base sequence given in SEQ ID NO: 6, this nucleic acid may be constituted of oligonucleotide that is composed of at least 13 consecutive bases in this base sequence or in a base sequence provided by the deletion, substitution, insertion, or addition of one or a plurality of bases in the base sequence described in SEQ ID NO: 6.

The polynucleotide constituting, e.g., the primer, probe, and so forth, may be immobilized on, e.g., a detection substrate. The detection substrate should be able to fix and hold the polynucleotide, and various materials, e.g., glass, plastic, fiber, and so forth, can be used. A microcarrier, e.g., a microarray, is an example of the configuration of the substrate material, and a disk shape and bead shape can be considered for its shape.

In the case of a multiplex assay, the surface of the microcarrier is preferably coded with a unique identifier, e.g., a bar code. For example, the microcarrier may contain (a) a layer that is a substantially transparent polymer layer having a first surface and a second surface, with the first and second surfaces being parallel to each other;

(b) a layer that is a substantially opaque polymer layer, wherein this substantially opaque polymer layer is affixed to the first surface of the substantially transparent polymer layer and encompasses a central region of the substantially transparent polymer layer and the substantially opaque polymer layer contains a two-dimensional shape that represents an analog code; and (c) a capture agent for capturing an analyte, wherein the capture agent is attached to at least one of the first surface and the second surface of the substantially transparent polymer layer, in at least the central region of the substantially transparent polymer layer.

Samples providing a target gene should be samples for which the presence of the target gene, or a bacterial species containing this gene, is suspected, but are not otherwise particularly limited, and can be exemplified by bodily fluids originating from a human or nonhuman, e.g., blood, serum, plasma, urine, feces, saliva, sputum, tissue fluids, cerebrospinal fluid, and swab fluids and their dilutions, wherein blood, serum, plasma, urine, feces, and cerebrospinal fluid and their dilutions are preferred. The sample may be, for example, a food, soil, a plant, and so forth.

Besides the primer and sample, a PCR buffer containing a DNA polymerase enzyme, substrates, and magnesium ion is also added to the reaction solution.

The PCR may be a singleplex assay that amplifies only the target gene or may be a multiplex assay that simultaneously amplifies the target gene and one or a plurality of other genes.

Multiplex assays, e.g., multiplex PCR, are known to the individual skilled in the art. πCode technology is a multiplex assay technology: this is a technology that enables simultaneous multi-item measurement through the identification of the type of a test target based on immobilization of a probe, for measuring an antibody or a gene, on a magnetic microdisc that is imprinted on its surface with a bar code. πCode technology is disclosed in, for example, WO 2016/198954 (Japanese Translation of PCT Application No. 2018-518146) and WO 2018/052464 (Japanese Translation of PCT Application No. 2019-535003), the contents of which are incorporated in their entirety in the present Description by reference.

The present invention is specifically described using the examples provided in the following, but the present invention is not limited to or by the examples.

EXAMPLES

Example 1: Comparison of the Results of Analysis, Using Normal PCR and Asymmetric PCR, Over a Substrate that Uses a DNA Probe Directed to the *Pseudomonas aeruginosa* Genome (1) Primer and Probe Design The primers given in SEQ ID NOs: 4 and 5 and the probe given in SEQ ID NO: 6 were designed based on the results, shown in FIG. 1, of multiple sequence alignment of the oprL genes (SEQ ID NOs: 1, 2, and 3) of *P. aeruginosa* strain E6130952, strain NCTC10332, and strain PAO1. The GC content of the oprL gene is 62.3%. These primers do not contain an inactivating chemical modification that is restored by the action of an activating enzyme.

(2) Nucleic Acid Amplification and Detection

Genomic DNA extracted from *Pseudomonas aeruginosa* strain JCM14847 was used as the template; normal PCR was carried out using a primer molar ratio between SEQ ID NO: 4 and SEQ ID NO: 5 of 1-to-1; asymmetric PCR was carried out using a primer molar ratio between SEQ ID NO: 4 and SEQ ID NO: 5 of 1-to-2.5; and an on-substrate hybridization reaction, labeling, and fluorescence measurement were carried out. A magnetic microcarrier (PlexBio Co., Ltd.) having a barcode imprinted on its surface was used as the substrate. A primer provided by biotin modification via a linker at the 5'-end of SEQ ID NO: 5 was used at this time.

A TaKaRa Multiplex Assay Kit Ver. 2 (Takara Bio Inc.) was used for amplification. In the normal PCR, each primer was added so as to provide a final concentration of 0.2 μM. In the asymmetric PCR, addition was made so the respective final concentrations were 0.2 UM and 0.5 μM. The template genomic DNA was added at 200 μg per 1 reaction. The 2× Reaction buffer in the TaKaRa Multiplex Assay Kit Ver. 2 was added to provide a final concentration of 1×, and the Multiplex Enzyme Mix was added to provide a final concentration of 1 U. A T100 Thermal Cycler (Bio-Rad Laboratories, Inc.) was used as the nucleic acid amplifying device. Using the same device, a thermal denaturation reaction was performed after the completion of the amplification reaction and before introduction to the on-substrate hybridization reaction.

The reagent used in the on-substrate hybridization reaction was prepared by mixing the following: a solution containing the substrate on which the SEQ ID NO: 6 probe, which captures the PCR product from *P. aeruginosa* strain JCM14847, had been immobilized, saline-sodium phosphate-EDTA buffer (SSPE buffer), and the PCR reaction solution post-thermal denaturation.

Streptavidin-phycoerythrin (PlexBio Co., Ltd.) was used in the reagent for labeling. An IntelliPlex 1000 πCode Processor (PlexBio Co., Ltd.) was used for the device for the on-substrate hybridization reaction and labeling. A PlexBio (registered trademark) 100 Fluorescent Analyzer (PlexBio Co., Ltd.) was used as the instrument for measuring the fluorescence.

The following conditions were used.

Amplification Reaction Conditions:

94° C. 30 seconds

60° C. 60 seconds→94° C. 30 seconds (number of cycles: 30)

72° C. 600 seconds

Thermal Denaturation Conditions:

95° C. 5 minutes→quenching to 4° C.

Hybridization Conditions:

37° C. incubation for 20 minutes

Labeling Conditions:

37° C. incubation for 10 minutes (3) Measurement Results

The results of the measurement are given in FIG. 2. For the use as the template of genomic DNA extracted from *P. aeruginosa* strain JCM14847, the fluorescence value provided by the asymmetric PCR was 87818, in contrast to the fluorescence value provided by the normal PCR of 27195. Based on this, it was shown that the application of asymmetric PCR to the detection of *P. aeruginosa* provided an approximately 3-fold increase in sensitivity.

Example 2: Difference Between Sensitization Effects for Asymmetric PCR in the Case of Use of Templates Having Different GC Contents (1) Nucleic Acid Amplification and Detection Genomic DNA extracted from *P. aeruginosa* strain JCM14847 was used as the template; normal PCR was carried out using a primer molar ratio between SEQ ID NO: 4 and SEQ ID NO: 5 of 1-to-1; asymmetric PCR was carried out using a primer molar ratio between SEQ ID NO: 4 and SEQ ID NO: 5 of 1-to-2.5; and an on-substrate hybridization reaction, labeling, and fluorescence measurement were carried out. A primer provided by biotin modification via a linker at the 5'-end of SEQ ID NO: 5 was used at this time.

For the first comparison target, genomic DNA extracted from *Staphylococcus epidermidis* strain JCM2414 was used as the template; normal PCR was carried out using a primer molar ratio for SEQ ID NOs: 7 and 8 of 1-to-1; asymmetric PCR was carried out using a primer molar ratio between SEQ ID NO: 7 and SEQ ID NO: 8 of 1-to-2.5; and an on-substrate hybridization reaction, labeling, and fluorescence measurement were carried out. A primer provided by biotin modification via a linker at the 5'-end of SEQ ID NO: 8 was used at this time.

For the second comparison target, genomic DNA extracted from *Proteus mirabilis* strain JCM1669 was used as the template; normal PCR was carried out using a primer molar ratio for SEQ ID NOs: 10 and 11 of 1-to-1; asymmetric PCR was carried out using a primer molar ratio between SEQ ID NO: 10 and SEQ ID NO: 11 of 1-to-2.5; and an on-substrate hybridization reaction, labeling, and fluorescence measurement were carried out. A primer provided by biotin modification via a linker at the 5'-end of SEQ ID NO: 11 was used at this time.

Finally, for the third comparison target, genomic DNA extracted from *Acinetobacter baumannii* strain JCM6841 was used as the template; normal PCR was carried out using a primer molar ratio for SEQ ID NOs: 13 and 14 of 1-to-1; asymmetric PCR was carried out using a primer molar ratio for between SEQ ID NO: 13 and SEQ ID NO: 14 of 1-to-2.5; and an on-substrate hybridization reaction, labeling, and fluorescence measurement were carried out. A primer provided by biotin modification via a linker at the 5'-end of SEQ ID NO: 14 was used at this time.

A TakaRa Multiplex Assay Kit Ver. 2 (Takara Bio Inc.) was used for amplification. In the normal PCR, each primer was added so as to provide a final concentration of 0.2 μM. In the asymmetric PCR, addition was made to provide a final concentration of 0.2 UM and a final concentration of 0.5 M. The template genomic DNA was added at 200 μg per 1 reaction. The 2× Reaction buffer in the TaKaRa Multiplex Assay Kit Ver. 2 was added to provide a final concentration of 1×, and the Multiplex Enzyme Mix was added to provide a final concentration of 1 U. A T100 Thermal Cycler (Bio-Rad Laboratories, Inc.) was used as the nucleic acid amplifying device. Using the same device, a thermal denaturation reaction was performed after the completion of the amplification reaction and before introduction to the on-substrate hybridization reaction.

The reagent used in the on-substrate hybridization reaction was prepared by mixing the following: a solution containing substrate on which the probe of SEQ ID NOs: 6, 9, 12, 15 had been immobilized, saline-sodium phosphate-EDTA buffer (SSPE buffer), and the PCR reaction solution post-thermal denaturation. Here, the probe with SEQ ID NO: 9 is a probe that captures the PCR product from *S. epidermidis*; the probe with SEQ ID NO: 12 is a probe that captures the PCR product from *P. mirabilis*; and SEQ ID NO: 15 is a probe that captures the PCR product from *A. baumannii.*

The reagent used for labeling, the equipment used for the on-substrate hybridization reaction and labeling, the fluorescence measurement instrumentation, and the various conditions are the same as in Example 1.

(2) Measurement Results

Figure 3:
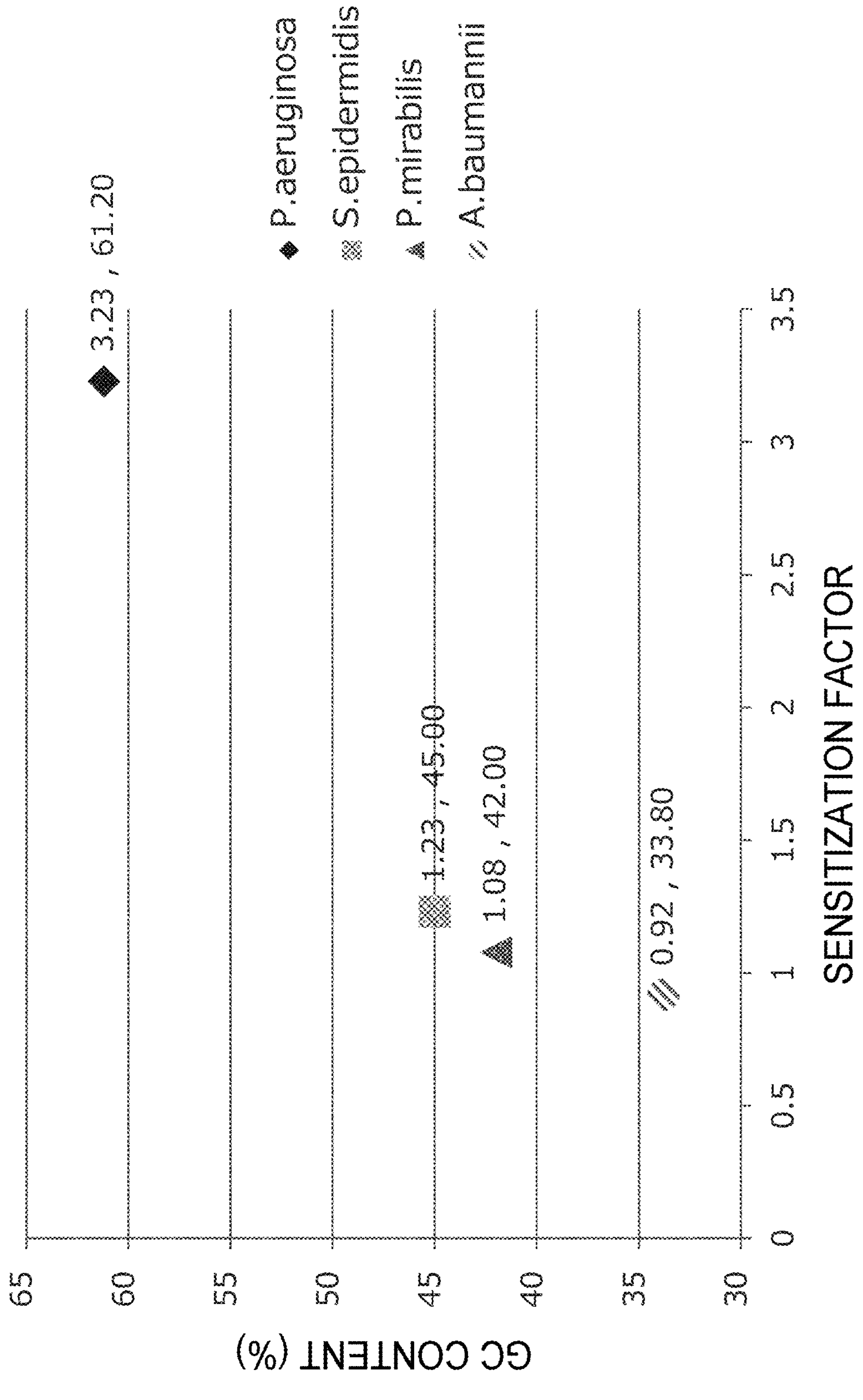
FIG. 3 shows the results for the sensitization factor for the amplification, using asymmetric PCR, of templates having GC contents different from that of genomic DNA extracted from *P. aeruginosa* strain JCM14847.
Figure 4:
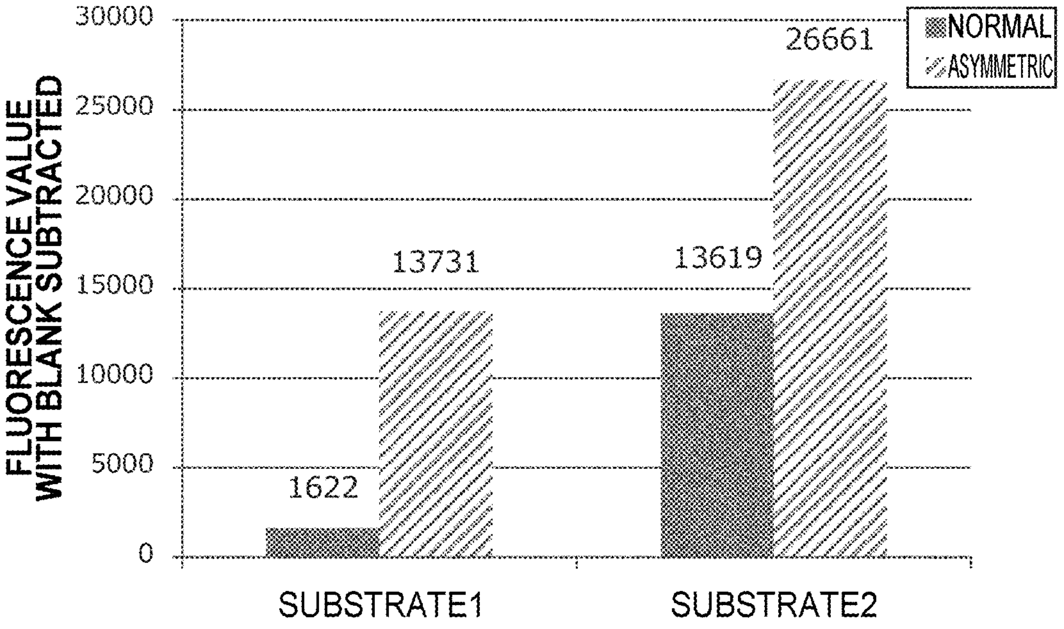
FIG. 4 shows the results of a comparison of the fluorescence values in normal PCR and asymmetric PCR carried out using as the template genomic DNA extracted from a culture medium that contained *P. aeruginosa* and *Enterococcus casseliflavus.*

FIG. 3 shows a plot of the results using the sensitization factor—which is the value provided by dividing the fluorescence value in the asymmetric PCR by the fluorescence value in the normal PCR—for the horizontal axis, and using the GC content of the PCR product for each item, represented by SEQ ID NOs: 16, 17, 18, and 19, for the vertical axis. Here, the sensitization factor refers to the numerical value provided by dividing the fluorescence value yielded by execution of the amplification reaction using asymmetric PCR and carrying out detection on the resulting amplification product, by the fluorescence value yielded by execution of the amplification reaction using normal PCR and carrying out detection on the resulting amplification product; a higher sensitization factor means a higher detection sensitivity over normal PCR. The following is shown based on the results in FIG. 3: for the case of a low GC content, the sensitization factor increases in accordance with the GC content; when the GC content of the target gene is at least 60%, there is a very substantial increase in the sensitization factor, i.e., the detection sensitivity.

As shown in FIG. 3, a positive correlation between the sensitization factor and GC content was confirmed. With regard to the reason for the appearance of this correlation, it is thought that the rate of a nucleic acid hybridization reaction exhibits a large dependence on the composition of the nucleic acid. The following model has been proposed for the hybridization reaction: some of the complementary bases repeatedly approach and separate between two molecules that have complementary sequences, and, when association with a completely complementary sequence eventually occurs, base pairs are formed that will close the zipper from there. It has been reported, according to results calculated using an 8-base model sequence, that the rate of base pair formation for a high-GC base sequence has been calculated to be 3.2-times that for a high-AT base sequence, and that a high-GC base sequence more rapidly associates with its complementary sequence and forms a complementary strand (DNA hybridization kinetics: zippering, internal displacement and sequence dependence. Nucleic Acids Res. 2013 October; 41(19):8886-8895).

The targets for on-substrate capture in this example are PCR products provided by amplification as double-stranded DNA and denaturation. Thus, it is thought that for the PCR product the hybridization reaction proceeds in a mode in which formation of a partial complementary strand with the on-substrate probe coexists with complementary strand formation with PCR product. The following is hypothesized based on the aforementioned measurement results: as the GC content of the product increases, the capture reaction by the probe, as well as PCR product-to-PCR product complementary strand formation, are both accelerated, and, while the capture reaction by the probe did not proceed satisfactorily in the normal PCR, the capture reaction by the probe proceeded effectively due to the excess production, through the application of asymmetric PCR, of molecules that are captured onto the substrate and a remarkable sensitizing effect was obtained.

With the low GC content *A. baumannii*, on the other hand, it was found that the fluorescence value was reduced, with a sensitization factor of 0.92, when asymmetric PCR was run. It is hypothesized, with regard to on-substrate detection, that two types of hybridization reactions are occurring—in the mode in which partial complementary chain formation with the probe already on the substrate coexists with complementary chain formation with PCR product—and in addition that numerous parameters, e.g., the number of molecules of capture targets, GC content, base pair formation rate, and so forth, are related and are reflected in the final fluorescence value. It is known that the PCR product yield in asymmetric PCR is lower than in normal PCR, and the present results show that asymmetric PCR can act unfavorably with low GC content target genes.

Based on the preceding, it has been demonstrated that the detection sensitivity is improved by the application of asymmetric PCR to the detection of a template having a GC content of at least 60%.

Example 3: Example of Simultaneous Detection of a Gene Having a GC Content of at Least 60% and a Gene without this Property (1) Nucleic Acid Amplification and Detection A sample 1 was prepared which was confirmed, by a culture and identification procedure, to contain two bacterial species, i.e., *Pseudomonas aeruginosa* (GC content of strain PA01: 66.6%) and *Enterococcus casseliflavus*. It is known that the GC content of *P. aeruginosa* strain PA01 is 66.6% and the GC content for *Enterococcus casseliflavus* is 42.9% (Sanderson, H., Ortega-Polo, R., Zaheer, R. et al., Comparative genomics of multidrug-resistant *Enterococcus* spp. isolated from wastewater treatment plants. BMC Microbiol 20, 20 (2020). https://doi.org/10.1186/s12866-019-1683-4).

Amplification by multiplex PCR was carried out using as template the genomic DNA extracted from the sample using a QIAamp BiOstic Bacteremia DNA Kit (QIAGEN) and using the standard protocol provided with the reagent, and an on-substrate hybridization reaction, labeling, and fluorescence measurement were also carried out. As in Examples 1 and 2, a magnetic microcarrier (PlexBio Co., Ltd.) having a barcode imprinted on its surface was used as the substrate. In addition, the reagent used for labeling, the on-substrate hybridization reaction, the instrument used for labeling, the fluorescence measurement instrument, and the other conditions are the same as in Examples 1 and 2, unless specifically indicated otherwise.

A TakaRa Multiplex Assay Kit Ver. 2 (Takara Bio Inc.) was used for amplification. With regard to the primers, the primers given by SEQ ID NOs: 4 and 5 were used for *Pseudomonas aeruginosa*, and the primers given by SEQ ID NOs: 20, 21, 22, and 23 were used for *Enterococcus casseliflavus*. In the normal PCR, each primer was added so as to provide a final concentration of 0.2 UM for all the primers. In the asymmetric PCR, addition was made so the final concentration for the primer other than SEQ ID NO: 5 was 0.2 UM and addition was made so the primer with SEQ ID NO: 5 had a final concentration of 0.5 μM. Primers provided by biotin modification via a linker at the 5'-end of SEQ ID NOs: 5 and 23 were used. The template solution was added at 5 μL per 1 reaction. The 2× Reaction buffer in the TakaRa Multiplex Assay Kit Ver. 2 was added to provide a final concentration of 1×, and the Multiplex Enzyme Mix was added to provide a final concentration of 1 U. A T100 Thermal Cycler (Bio-Rad Laboratories, Inc.) was used as the nucleic acid amplifying device. Using the same device, a thermal denaturation reaction was performed after the completion of the amplification reaction and before introduction to the on-substrate hybridization reaction.

The reagent used in the on-substrate hybridization reaction was prepared by mixing the following: a solution containing a substrate 1 on which a probe (SEQ ID NO: 6) that captured *Pseudomonas aeruginosa* had been immobilized, and containing a substrate 2 on which a probe (SEQ ID NO: 24) that captured *Enterococcus casseliflavus* had been immobilized; saline-sodium phosphate-EDTA buffer (SSPE buffer); and the PCR reaction solution post-thermal denaturation.

For substrate 1, on which a probe that captured *Pseudomonas aeruginosa* had been immobilized, the fluorescence values provided by subtracting the blank were 1622 for the normal PCR and 13731 for the use of asymmetric PCR, and the detection sensitivity was thus substantially improved. For substrate 2, on which a probe that captured *Enterococcus casseliflavus* had been immobilized, the detection sensitivity was also satisfactorily high for the normal PCR, while a negative effect was also not exercised on the results for substrate 1 for the amplification of *Pseudomonas aeruginosa* by asymmetric PCR, and the detection sensitivity was also raised according to the results for substrate 2.

Thus, asymmetric PCR also worked effectively for the simultaneous detection of a gene having a GC content of at least 60% and a gene without this property, and the efficacy of the present invention could be confirmed.

What is claimed is:

1. A method for amplifying, in a reaction solution, at least one target gene having a GC content of at least 60% and one or more genes that are not the at least one target gene, the method comprising:

amplifying specific base sequences in the at least one target gene and the one or more genes that are not the at least one target gene by using a first primer set comprising a first primer and a second primer for target gene amplification and a second primer set comprising one or more forward primers and one or more reverse primers for amplification of the one or more genes that are not the at least one target gene, wherein, in amplifying, one primer in the first primer set is added to the reaction solution at a molar concentration higher than the other primer in the first primer set, and the one or more forward primers in the second primer set are added at the same concentration as the one or more reverse primers in the second primer set, and neither the first or second primer is a hot start primer that contains an inactivating chemical modification that is restored by an action of an activating enzyme.

2. The method according to claim 1, wherein the molar ratio of the primers in the first primer set is 1:1.5 to 3.5.

3. The method according to claim 1, wherein a target gene is a base sequence consisting of at least 13 consecutive bases in the genomic sequence of *Pseudomonas aeruginosa.*

4. The method according to claim 1, wherein the first primer is a primer that hybridizes, under stringent conditions, with a base sequence set forth in any of SEQ ID NOs: 1 to 3, and the second primer is a primer that hybridizes, under stringent conditions, with a complementary strand sequence of a base sequence set forth in any of SEQ ID NOs: 1 to 3.

5. The method according to claim 1, wherein the first primer is an oligonucleotide consisting of at least 13 consecutive bases in the base sequence set forth in SEQ ID NO: 4.

6. The method according to claim 1, wherein the second primer is an oligonucleotide consisting of at least 13 consecutive bases in the base sequence set forth in SEQ ID NO: 5.

7. The method according to claim 1, wherein a primer in the first primer set is labeled with biotin.

8. The method according to claim 1, wherein the primer in the first primer set with the higher molar concentration is labeled with biotin.

9. The method according to claim 1, wherein the at least one target gene originates from *Pseudomonas aeruginosa* and a bacterial gene from other than *Pseudomonas aeruginosa* is differentiated from *Pseudomonas aeruginosa.*

10. A method of detecting, in one reaction solution, at least one target gene having a GC content greater than 60%, the method comprising:

detecting the at least one target gene by using a probe that is complementary to a single strand of the at least one target gene that has been amplified by the method described in claim 1.

11. The method according to claim 10, wherein the probe is complementary to a single strand of the at least one target gene that has been amplified by the primer in the first primer set with the higher molar concentration.

12. The method according to claim 10, wherein the least one target gene is detected through occurrence of complementary double-stranded gene formation from the probe and the single strand of the at least one target gene.

13. The method according to claim 10, wherein the probe is immobilized on a detection substrate material.

14. The method according to claim 13, wherein the detection substrate material is a coded microcarrier.

15. The method according to claim 14, wherein the microcarrier comprises:

(a) a layer that is a substantially transparent polymer layer having a first surface and a second surface, with the first and second surfaces being parallel to each other;

(b) a layer that is a substantially opaque polymer layer, this substantially opaque polymer layer being affixed to the first surface of the substantially transparent polymer layer and encompassing a central region of the substantially transparent polymer layer, and the substantially opaque polymer layer containing a two-dimensional shape that represents an analog code; and (c) a capture agent for capturing an analyte, the capture agent being attached to at least one of the first surface and the second surface of the substantially transparent polymer layer, in at least the central region of the substantially transparent polymer layer.

16. The method according to claim 10, wherein the probe is labeled.

17. The method according to claim 10, wherein the probe comprises an oligonucleotide consisting of at least 13 consecutive bases in the base sequence set forth in SEQ ID NO: 6.

* * * * *